United States Patent [19]

Ring

[11] 4,286,595
[45] Sep. 1, 1981

[54] COMPACT TAMPON APPLICATOR ASSEMBLY

[75] Inventor: David F. Ring, Morganville, N.J.

[73] Assignee: Johnson & Johnson Products, Inc., New Brunswick, N.J.

[21] Appl. No.: 79,609

[22] Filed: Sep. 27, 1979

[51] Int. Cl.³ .............................................. A61F 15/00
[52] U.S. Cl. .................................................... 128/263
[58] Field of Search ..................... 128/263, 270, 285

[56] References Cited

U.S. PATENT DOCUMENTS

| | | | |
|---|---|---|---|
| 2,829,646 | 4/1958 | Kurkjian | 128/263 |
| 3,101,713 | 8/1963 | Sargent | 128/263 |
| 3,628,533 | 12/1971 | Loyer | 128/263 |

FOREIGN PATENT DOCUMENTS 700840  12/1964  Canada .................................... 128/263

*Primary Examiner*—John D. Yasko
*Attorney, Agent, or Firm*—Jason Lipow

[57] ABSTRACT

A tampon-applicator assembly of reduced length is provided comprising an outer tube, an inner tube nested therein and a tampon enclosed within said inner tube. A gripping portion affixed to the distal end of said inner tube is provided for reciprocating said inner tube almost completely out of the distal end of said outer tube while a restraining element is provided for restraining the tampon from being reciprocated with said inner tube. A deflecting portion is also provided at the distal end of the outer tube for deflecting at least a portion of the walls of the proximal end of the inner tube toward the center of the distal end of the tampon, when said inner tube is reciprocated. In operation, the inner tube is reciprocated out of the distal end of the outer tube, the tampon is restrained and hence transferred to the outer tube and the proximal walls of the inner tube are deflected toward the distal end of the tampon. The inner tube may now be reciprocated back toward the proximal end and the deflected walls will bear against and expel the tampon.

1 Claim, 15 Drawing Figures

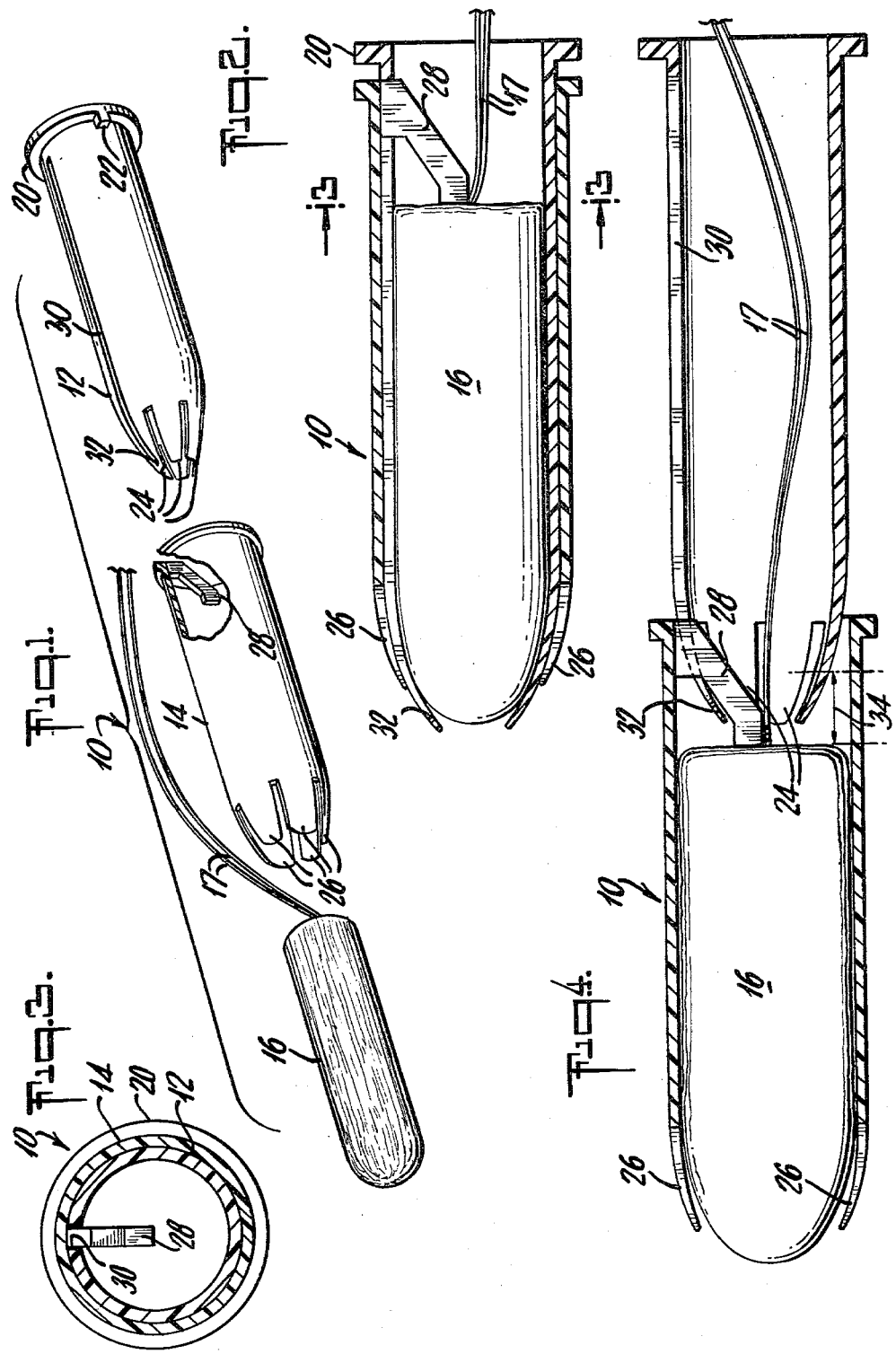

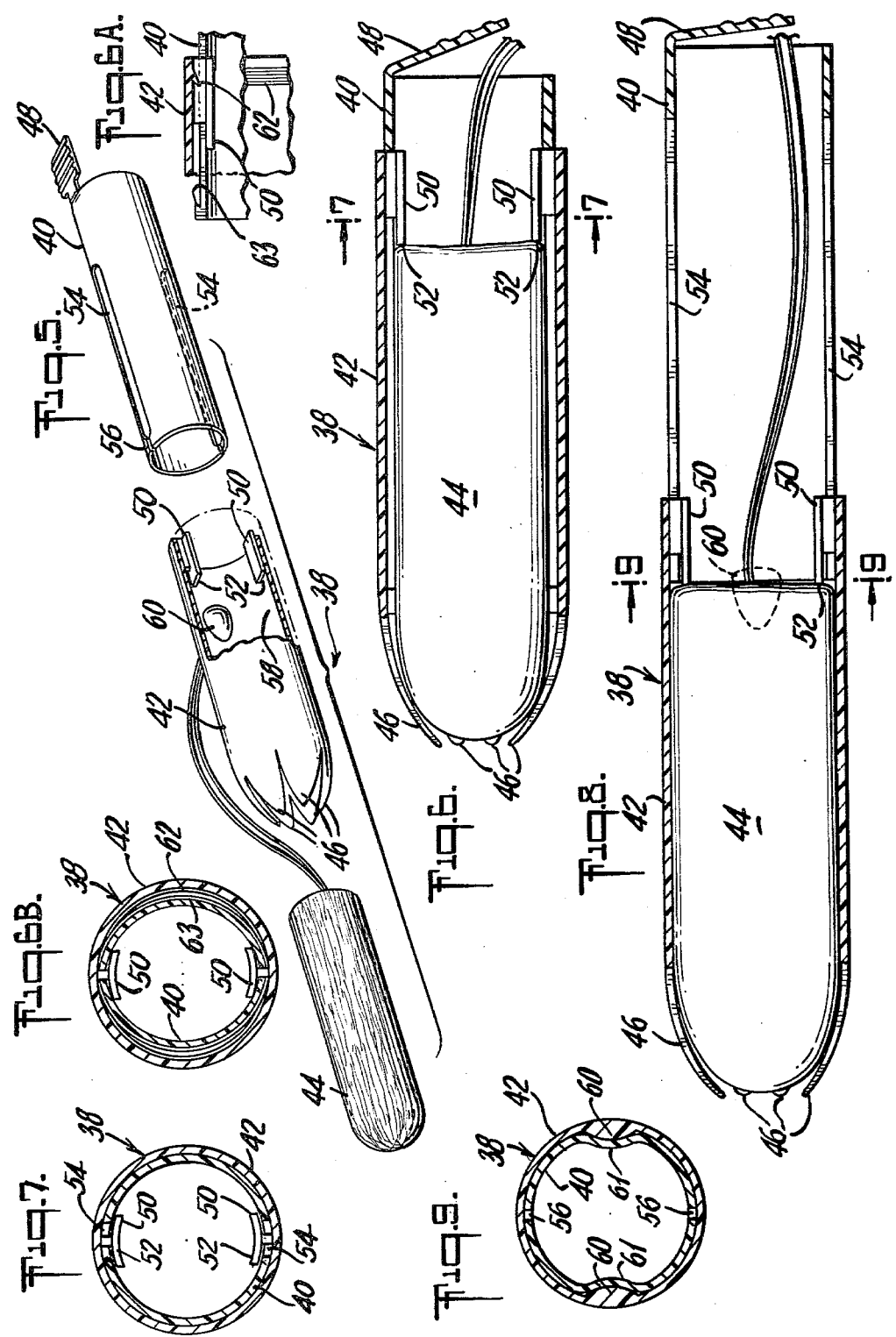

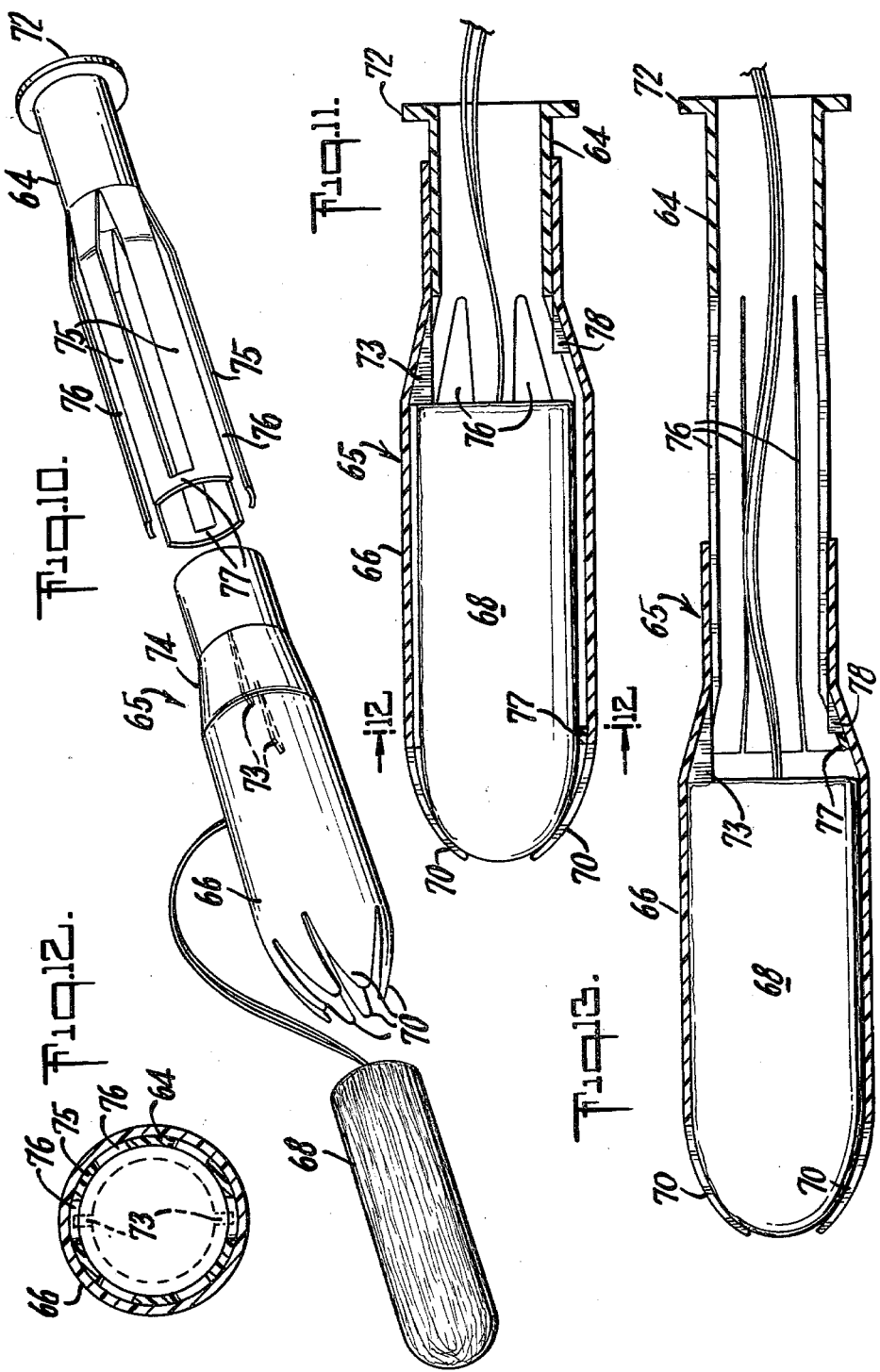

COMPACT TAMPON APPLICATOR ASSEMBLY

BACKGROUND OF THE INVENTION

This invention relates to tampon-applicator assemblies and is particularly directed toward such assemblies provided in a compact, unobtrusive, conveniently short form.

Many applicators for introducing catamenial tampons intervaginally have been suggested in the art and several are now on the market. The kind in widest use comprises an open ended tubular holder containing the tampon and is combined with a plunger adapted to slideably expel the tampon from the holder. The plunger is also generally tubular, though smaller in diameter than the holder, and is telescopically positioned therein so that by moving the plunger into one end of the holder, the tampon may be ejected from the opposite end. The holder is, of necessity, longer than the tampon and, to insure complete ejection of the tampon from the holder, generally the plunger is likewise longer than the holder. Consequently, the overall length of the holder and plunger assembly is always more than twice the length of the tampon.

Several drawbacks are associated with such prior tampon applicator assemblies. To provide sufficient assemblies for a menstrual period, it is customary to package a number of these, e.g., ten, in a single container. From the foregoing description, it is apparent that the tampon applicators and hence the containers used to package them are comparatively large with respect to the article, i.e., the tampon, ultimately used by the consumer. The necessity for large containers greatly adds to the cost of the marketed product, such added cost being particularly important in products of the kind herein considered, i.e., products intended for a single use and thereafter discarded. Accordingly, there is an economic incentive for a reduction in product size.

Perhaps even more importantly, a size reduction is advantageous from both a convenience and an aesthetic point of view. Finally, the product should be small enough to be conveniently carried in a woman's purse. Secondly, from an aesthetic viewpoint, a shorter more compact product is less noticeable and hence less embarrassing.

The prior art now abounds with suggestions of prior investigators for avoiding this problem of excessive length. I believe that none of these prior suggestions has reached commercial fruition primarily because of shortcomings in such designs which add cost, complexity or functional inconvenience to the product.

In a series of prior art suggestions (see for example, U.S. Pat. Nos. 3,115,876; 3,424,159; 3,059,642; 3,034,508; 3,103,929; 3,831,605; 3,090,385) it has been suggested that the plunger and holder be provided in assembled form or hinged together so that they may be packaged side by side, thereby substantially reducing the overall length of the packed tampon-applicator assembly. Such designs have not met with commercial success and, it is believed this is because, in addition to the complexity and expense in manufacturing the products, the user does not wish to be faced with the added operation of reassembling the plunger/holder combination into the operable configuration.

Another approach to a solution for the problem of excessive length is exemplified by U.S. patent application Ser. No. 833,201, filed on Sept. 14, 1977, by Michael Loyer. In accordance with this method, the tampon enclosed or partially enclosed within a holder is provided with an inner, axially extending bore in which the plunger resides prior to use. In use, the plunger is first pulled or screwed out of the bore, then locked in place and reciprocated toward the tampon to eject the same from the holder. While the operation of this kind of applicator assembly is relatively simple, unfortunately the concept involves a specially designed tampon having the required inner bore. Both because of the added difficulty of manufacturing such a tampon at high speed and because of the disadvantageous functional consequences resulting from a tampon of this kind, the solution suggested by Loyer has not been satisfactory.

Still another suggestion for solving the excessive length problem is exemplified by U.S. Pat. Nos. 2,832,342 and 3,101,713. This concept involves providing a tampon applicator assembly comprising two concentric tubes, providing one such tube nested within the other, and having the tampon provided within the inner tube. The inner tube is then reciprocated axially almost completely out of the outer tube and means are provided for preventing the tampon from being reciprocated along with the inner tube. Accordingly, when the inner tube is in its reciprocated position, the tampon now resides within the outer tube and along side the inner tube. The inner tube is then reciprocated toward the tampon and hence acts as a plunger for expelling the tampon from the remote end of the outer tube.

The problem with this suggestion is that in order for the inner tube to act as a plunger, the inner tube must in some way bear against the tampon. In both of the above-described patents, this is accomplished by selecting a tampon and sizing the diameters and thicknesses of the inner and outer tubes in such manner that when the tampon is transferred from the inner tube to the outer tube, the tampon expands in diameter to fill the outer tube. Accordingly, with the tampon now having a diameter equal to the inside diameter of the outer tube and also equal to the outside diameter of the inner tube, the walls of the inner tube will bear against the peripheral portions of the end of the tampon during the expulsion step.

There are several drawbacks encountered by this technique of obtaining bearing surface for the plunger. Firstly, the method is only applicable to relatively resiliently compressed tampons. In contrast thereto, the highly compressed cellulosic tampons do not generally have the resiliency to spring back and fill the outer tube upon being released from the inner tube. Secondly, the necessity of providing the tampon in a resilient compressed state also implies that the tampon in the packed state will be exerting pressure on the walls of the inner tube and, after this inner tube is retracted, on the walls of the outer tube. This pressure substantially increases the frictional resistance generated between the walls of the respective tubes and the tampon when retracting the tampon from the inner tube and expelling the tampon from the outer tube. It is highly undesirable to have any substantial resistance to these operations and, in fact, the frictional resistance should ideally be no more than is required for holding the tampon within the applicator assembly prior to use.

In view of the above, no completely satisfactory system has heretofore been devised for solving the excessive length problem.

SUMMARY OF THE INVENTION

In accordance with this invention, a tampon-applicator assembly is provided which overcomes the shortcomings of the art and provides such assembly in reduced length form without increased expense in manufacturing or increased inconvenience in use.

Specifically, a tampon-applicator assembly is provided having a proximal end and a distal end. As used herein, the term "proximal end" is meant to describe those portions of the assembly and its parts which are closest to the user's body when the tampon is emplaced within the vagina. The term "distal end" is meant to describe those portions of the assembly and its parts that are most remote from the body when the tampon is being emplaced.

The assembly comprises a generally cylindrical outer tube and a generally cylindrical inner tube. The inner tube has an outside diameter that is slightly less than the inside diameter of the outer tube and is snuggly nested and coaxially aligned within the outer tube. A tampon is provided, enclosed and coaxially aligned within the inner tube. It is preferred that the inner and outer tubes are both of approximately the same length and that such length is only slightly longer than the length of the tampon. Thus when the two tubes are nested and the tampon is enclosed within the inner tube, the entire assembly, now in the configuration presented to the user prior to use, will be only slightly longer than the tampon.

The distal end of the inner tube is provided with a gripping portion which extends out of the distal end of the outer tube when the inner tube is nested therein. The gripping portion is adapted to be gripped by the user to reciprocate the inner tube almost completely out of the distal end of the outer tube thereby placing the assembly into the tampon insertion position. This gripping portion, for example, may be merely an extended part of the inner tube or, alternatively, may be a flange on the distal end of the inner tube, a tab extending from the inner tube or any other of such similar elements as will occur to one skilled in the art.

At least one restraining element is provided in the outer tube and, specifically, in the distal half of the inside wall of the outer tube. The restraining element is adapted to bear against the distal end of the tampon and prevent the tampon from moving together with the inner tube, when the inner tube is reciprocated into the insertion position. Accordingly, when the inner tube is so reciprocated and the tampon restrained, the tampon will effectively transfer from a position of being immediately enclosed by the inner tube to the position of being immediately enclosed by the outer tube.

The restraining element may take various configurations. For example, a simple projection extending from the inner wall of the outer tube will suffice. In such case, it is necessary to insure that the inner tube can readily be reciprocated passed this restraining device while the tampon is being restrained. In a specific embodiment described herein the wall of the inner tube is provided with two axially extending slots for receiving two restraining elements. In an alternative embodiment the restraining element is no more than a portion of the distal end of the outer tube having a constricted diameter which will retard the movement of the tampon but will allow the inner tube to pass through. Again, the construction of the inner tube may be modified to facilitate its passing through such a constricted area.

In accordance with the teachings of this invention, the distal end of the outer tube is provided with a deflecting portion adopted to have at least a portion of the walls of the proximal end of the inner tube deflect toward the center of the distal end of the tampon when the inner tube has been reciprocated into the insertion position. In various specific embodiments, the deflecting portion may take various forms such as, for example, a projection over which a deformable inner tube rides when reciprocated and deforms into an out-of-round cross section. It will be understood that such deformation will bring parts of the proximal end of the inner tube closer toward the center of the distal end of the tampon. Alternatively, a constricted diameter portion in the distal end of the outer tube may be used to deflect the proximal end portion of the inner tube. In still another embodiment, the walls of the inner tube may be spring biased to deflect inwardly when free of the tampon (i.e., when moved to the insertion position) and the deflecting portion will simply be a distal portion at the end of the outer tube which provides clearance for such deflection.

In use then, the tampon-applicator assembly is presented in the compacted state. The user places the assembly in the insertion position by simply gripping the gripping portion and reciprocating the inner tube away from the outer tube. The assembly is now in the insertion position with the tampon transferred into the proximal end of the outer tube and with the inner tube directly behind the tampon. Because of the deflecting portion, the proximal walls of the inner tube are deflected toward the center of the distal end of the tampon to bear against the tampon. By simply pushing the inner tube toward her body, the user can expel the tampon.

BRIEF DESCRIPTION OF THE DRAWINGS

FIG. 1 is an exploded, prospective view of a first embodiment of the tampon-applicator assembly of this invention;

FIG. 2 is a longitudinal cross-sectional view of the assembly of FIG. 1 shown in the collapsed state and taken through the longitudinal axis thereof;

FIG. 3 is a cross-sectional view of the assembly of FIG. 2 taken through line 3—3;

FIG. 4 is a longitudinal cross-sectional view of the assembly of FIG. 1 shown in the insertion position and taken through the longitudinal axis thereof;

FIG. 5 is an exploded, prospective view of a second embodiment of the tampon-applicator assembly of this invention;

FIG. 6 is a longitudinal cross-sectional view of the assembly of FIG. 5 shown in the collapsed state and taken through the longitudinal axis thereof;

FIGS. 6(a) and 6(b) are slight modifications of the assembly shown in FIGS. 6 and 7 with identical parts bearing the same reference numbers;

FIG. 7 is a cross-sectional view of the assembly of FIG. 6 taken through line 7—7;

FIG. 8 is a longitudinal cross-sectional view of the assembly of FIG. 5 shown in the insertion position and taken through the longitudinal axis thereof;

FIG. 9 is a cross-sectional view of the assembly of FIG. 8 taken through line 9—9;

FIG. 10 is an exploded, prospective view of another embodiment of the tampon-applicator assembly of this invention;

FIG. 11 is a longitudinal cross-sectional view of the assembly of FIG. 10 shown in the collapsed state and taken through the longitudinal axis thereof;

FIG. 12 is a cross-sectional view of the assembly of FIG. 11 taken through line 12—12; and FIG. 13 is a longitudinal cross-sectional view of the assembly of FIG. 10 shown in the insertion position and taken through the longitudinal axis thereof.

DETAILED DESCRIPTION OF THE INVENTION

Referring now to FIGS. 1 through 4, shown there is a first embodiment of the tampon-applicator assembly 10 of this invention. FIG. 1 illustrates, in exploded perspective view the major components of the assembly, namely, an inner tube 12 and an outer tube 14, and a catamenial tampon 16. The tampon 16 is provided with the usual withdrawal string 17. The assembly and its components are shown in the drawings with the proximal end on the reader's left and the distal end of the reader's right. Both the inner and outer tubes comprise thin walled cylinders, open at both ends and each only somewhat larger than the tampon 16 with respect to length and diameter. The inner tube 12 is of a sufficiently smaller diameter than the outer tube so as to be able to snugly nest within the outer tube in the configuration shown in FIGS. 2, 3 and 4. By snugly nesting, it is meant that the inner tube fits tightly enough to avoid unintended dislodging when the assembly is in the collapsed position as shown in FIG. 2 while, at the same time, is loose enough so as to be easily reciprocated into the tampon insertion position as shown in FIG. 4 and not offer untoward resistance when the tampon is being inserted from this position.

As is shown in FIG. 2, the inner tube 12 is nested within the inner tube 14 and the tampon 16 is enclosed within the inner tube. The tampon-applicator assembly in this configuration, which is the one presented to the user prior to use, is only slightly longer than the tampon 16 itself. The withdrawal string 17 is extended out of the distal end of the assembly so that the user can assure herself that the string is firmly attached to the tampon prior to inserting the same.

The proximal ends of both inner and outer tubes terminate in sets of petals 24 and 26, respectively. These petals are flexibly biased toward the axis of the tubes and, as shown in FIG. 2, are adapted to protect and cover the tampon when the assembly is in the collapsed position. On the other hand, the petals 26 of the outer tube are also the leading surface into the body when the tampon is to be inserted with the assembly in the insertion position as is illustrated in FIG. 4. Accordingly, the petals 26 are adapted to present a smooth, domed, leading surface to minimize the user's discomfort during insertion.

The distal end of the inner tube 12 is provided with a gripping portion which extends out of the distal end of the outer tube 14 when the assembly is in the collapsed state and is adapted to be gripped by the user to reciprocate the inner tube almost completely out of the outer tube and place the assembly into the insertion position shown in FIG. 4. In the embodiment illustrated, the gripping portion comprises a ring 20, circumscribing the extreme distal portion of the outer periphery of the inner tube 12. To make this ring accessible for gripping, a spacing projection 22 is provided on the outer wall of the inner tube to keep the ring spaced away from the outer tube 14.

By gripping the outer tube in one hand and the ring 20 of the inner tube in the other, the assembly may be placed into the insertion position shown in FIG. 4. In accordance with this invention, when the inner tube is so reciprocated means are provided for restraining the tampon 16 from reciprocating along with the inner tube 12. In the embodiment illustrated in FIGS. 1-4, these means comprise a restraining element 28 provide at the distal end of the outer tube to bear against the distal end of the tampon 16 and restrain the tampon from moving toward the distal end of the outer tube. Accordingly, as the inner tube is reciprocated out of the outer tube, the tampon is restrained and, in effect, is transferred from the inner tube to the outer tube. Preferably the restraining element 28 is sufficiently flexible to allow the tampon to be loaded into the inner tube from the distal end thereof. The angular shape of element 28, as dipicted in FIGS. 1-4 also facilitates distal end tampon loading.

In order to allow the inner tube 12 to pass by the restraining element 28, a slot 30 is provided extending longitudinally through the wall of the inner tube 12. The restraining element 28 may then be fitted into slot 30 and hence the inner tube will be free to move relative thereto. Additionally, the combination of the restraining element and the slot will prevent the inner tube from undesirable rotation. By having the slot fall short of the extreme end of petals 24, a slot end surface 32 is provided which, in cooperation with restraining element 28, will prevent the inner tube from unintentionally being reciprocated completely out of the outer tube. In this connection, by preferably providing element 28 with sufficient flexibility, the inner tube may be assembled togather with the outer tube without the need for careful registration of the slot 30 with the element 28. After assembly, the inner tube may be rotated to engage element 28 into slot 30.

Referring to FIG. 4, with the assembly now in the insertion position, the inwardly biased petals of the inner tube will tend to deflect toward the axis of the tubes and hence in a direction toward the center of the distal end of the tampon. To facilitate this, a deflecting portion 34 is provided at the distal end of the outer tube and, in the embodiment shown, deflecting portion 34 is merely an additional length which will allow sufficient clearance for the petals 24 of the inner tube to deflect toward the center of the distal end of the tampon. The petals 24, now deflected, will bear against the tampon and allow the user to insert the same by reciprocating the inner tube.

Referring now to FIGS. 5 through 9, shown there is a second embodiment of the tampon-applicator assembly 38 of this invention. FIG. 5 illustrates, in exploded, perspective view the major components, namely an inner tube 40, an outer tube 42 and a catamenial tampon 44. As is best viewed in FIG. 6, when the assembly is in the collapsed state, the inner tube 40 is sized and adapted to fit snugly within the outer tube 42 with the tampon 44 enclosed within the inner tube. As in the previous embodiment, the proximal end of the outer tube is provided with a set of petals 46 presenting a smooth, domed, leading surface to minimize user's discomfort.

The distal end of the inner tube 40 is provided with a gripping portion which extends out of the distal end of the outer tube 42 when the assembly is in a collapsed state and is adapted to be gripped by the user to reciprocate the inner tube almost completely out of the outer tube and place the assembly into the insertion position shown in FIG. 8. In the embodiment illustrated, the gripping portion consists of a tab 48 extending from the extreme distal end of the inner tube.

By gripping the tab in one hand and the outer tube in the other, the user may reciprocate the assembly into the insertion position shown in FIG. 8 and transfer the tampon from the inner tube to the outer tube.

As described above, in order to accomplish this transfer, restraining means 50 are provided and in this embodiment comprise T-shaped projections depending from the distal end of the inner wall of the outer tube. Upon reciprocating the assembly into the insertion position, the tampon will bear against the proximal end 52 of the restraining means 50 and be prevented from reciprocating with the inner tube.

To allow the inner tube 40 to pass by restraining element 50, slots 54 are provided extending longitudinally through the walls of the inner tube. The restraining element 50 may be fitted into slot 54 and hence allow the inner tube to reciprocate past the restraining element. To prevent the inner tube from being reciprocated entirely out of the outer tube, the proximal end of slot 54 is provided with shoulders 56 to bear against restraining element 50 when only a short length of the inner tube still resides within the outer tube.

In accordance with this invention, when the inner tube is reciprocated into the insertion position, the proximal end now resides within the deflecting portion 58 wherein the walls of the proximal end of the inner tube are deflected toward the center of the distal end of the tampon. In the illustrated embodiment, this is accomplished by providing at least one deflection element 60 which is a raised surface extending inwardly from the inner wall of the outer tube in the deflecting portion 58 of the outer tube. As is best viewed in FIGS. 8 and 9, this raised portion constricts the proximal end of the inner tube and forces it out of round. Said in other words, wall portions 61 of the proximal end of the inner tube are deflected toward the distal end of the tampon. When the tampon is to be inserted and the inner tube is reciprocated toward the user's body, these portions 61 will bear against the distal end of the tampon and expel the tampon.

In FIGS. 6a and 6b (essentially the same illustration as FIGS. 6 and 7 with equivalent parts bearing the same reference numbers) the deflection element 60 is replaced with deflecting ring 62 which serves not only to deflect the walls of the inner tube against the tampon but also to restrain the inner tube from being unintentionally reciprocated totally out of the outer tube. This is accomplished by providing bearing ring 63 on the proximal end of the inner tube which co-operates with deflecting ring 62 to prevent the inner tube from being reciprocated out of the outer tube.

Referring now to FIGS. 10 through 14, shown there is still another embodiment of this invention, tampon-applicator assembly 65. FIG. 10 illustrates in exploded, perspective view the major components; an inner tube 64, an outer tube 66 and a catamenial tampon 68. Referring specifically to FIG. 11, when the assembly is in the collapsed state, the inner tube 64 is sized and adapted to fit snugly within the outer tube 66 with the tampon 68 enclosed within the inner tube. Again, the proximal end of the outer tube is provided with a set of domed petals 70 for user's comfort.

The distal end of the inner tube 64 is provided with a gripping portion which extends out of the distal end of the outer tube 66 when the assembly is in a collapsed state. In this embodiment the gripping portion comprises a flange 72 projecting circumferentially from the extreme distal end of the inner tube.

The user may, by gripping the flange 72 in one hand and the outer tube in the other, reciprocate the assembly into the insertion position shown in FIG. 13, and transfer the tampon from the inner tube to the outer tube. Once again, to accomplish this transfer, a restraining means 74 is provided and means 74 could be no more than a constricted portion of the outer tube having a lesser diameter than the tampon. In the embodiment shown, fins 73 are provided depending from the wall of the outer tube and further acting to restrain the tampon. Upon reciprocating the assembly into the insertion position, the tampon will bear against these fins and be prevented from reciprocating with the inner tube.

The inner tube 64 on the other hand can easily pass the fins 73 and the restraining means 74 as this tube consists essentially of alternating slots 76 and flexible fingers 75. As this inner tube 64 is reciprocated toward the distal end of the outer tube, the portions of the inner tube passing through the restraining means 74 collapse to allow passage therethrough.

In accordance with this invention, when the inner tube is reciprocated and the assembly is in the insertion position, the proximal end of the inner tube is deflected toward the distal end of the tampon in a deflecting portion. In the embodiment illustrated in these FIGS. 10-14, the restraining element 74 and the deflecting portion are the same constricted portion of the outer tube. When the proximal ends of the fingers 76 making up the walls of the inner tube reach the restraining element 74, they are, by virtue of the reduced diameter and in combination with the flexibility of the fingers, deflected toward the center of the distal end of the tampon. Accordingly, when the inner tube is then reciprocated toward the user's body to insert the tampon, the proximal end of these fingers will bear against and expel the tampon.

The inner and outer tubes of the tampon-applicator assemblies of this invention may be constructed of various materials such as paper board, synthetic polymers or the like. Preferably, they are constructed of moldable polymers with polypropylene or polyethylene being the materials of choice.

While this invention has been described in terms of certain specific embodiments, it will be appreciated by those skilled in the art that many variations are possible while still adhering to the teachings herein. In particular, it will be understood that features taken from each of the illustrated embodiments may be variously combined to form different embodiments and still be within the scope of this invention.

What is claimed is:

1. In a tampon applicator assembly having a proximal end and a distal end and comprising:
   a generally cylindrical outer tube;
   a generally cylindrical inner tube having an outside diameter less than the inside diameter of said outer tube, said inner tube being snugly nested, coaxially within said outer tube;
   a tampon enclosed coaxially within said inner tube;
   a gripping portion affixed to the distal end of said inner tube for gripping said inner tube and reciprocating said tube almost completely out of said distal end of said outer tube;
   at least one restraining element in the distal half of the outer tube for restraining said tampon from reciprocating with said inner tube so that the tampon will remain enclosed by said outer tube when said inner tube is reciprocated; and a deflecting portion at the distal end of said outer tube for deflecting at least a portion of the walls of the proximal end of the inner tube toward the center of the distal end of the tampon;

whereby when said inner tube is so reciprocated, said tampon will be transferred to said outer tube and when said reciprocated inner tube is then urged toward said proximal end of the assembly, the portion of the wall of said inner tube deflected toward the center of the end of the tampon will bear against said end and expel said tampon;

the improvement wherein: said restraining element is a T-shaped projection.

* * * * *